US008280699B2

(12) United States Patent
Ichishima et al.

(10) Patent No.: US 8,280,699 B2
(45) Date of Patent: Oct. 2, 2012

(54) MOLECULAR SIMULATING METHOD, MOLECULAR SIMULATION DEVICE, MOLECULAR SIMULATION PROGRAM, AND RECORDING MEDIUM STORING THE SAME

(75) Inventors: Daiji Ichishima, Yokosuka (JP); Yoshitaka Ohnishi, Yokosuka (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 243 days.

(21) Appl. No.: 12/670,164

(22) PCT Filed: May 16, 2008

(86) PCT No.: PCT/JP2008/059054
§ 371 (c)(1),
(2), (4) Date: Jan. 22, 2010

(87) PCT Pub. No.: WO2009/016873
PCT Pub. Date: Feb. 5, 2009

(65) Prior Publication Data
US 2010/0211366 A1 Aug. 19, 2010

(30) Foreign Application Priority Data

Jul. 31, 2007 (JP) ................................. 2007-199646

(51) Int. Cl.
*G06F 17/50* (2006.01)
*G06F 7/60* (2006.01)
*G06G 7/48* (2006.01)
*G06G 7/58* (2006.01)

(52) U.S. Cl. .......... 703/1; 703/2; 703/6; 703/11; 703/12

(58) Field of Classification Search .................. 703/1, 2, 703/6, 11, 12
See application file for complete search history.

(56) References Cited

U.S. PATENT DOCUMENTS

| | | | | |
|---|---|---|---|---|
| 5,265,030 A * | 11/1993 | Skolnick et al. | ................ | 703/11 |
| 5,526,281 A * | 6/1996 | Chapman et al. | ................ | 702/22 |
| 5,619,421 A * | 4/1997 | Venkataraman et al. | ........ | 702/27 |
| 5,699,268 A * | 12/1997 | Schmidt | .......................... | 702/27 |
| 5,703,792 A * | 12/1997 | Chapman | ........................ | 506/24 |
| 5,796,632 A * | 8/1998 | Yuta | .................................. | 702/27 |
| 5,937,094 A * | 8/1999 | Nagasawa | ..................... | 382/232 |
| 6,051,029 A * | 4/2000 | Paterson et al. | .................. | 703/22 |
| 6,070,127 A * | 5/2000 | Hirono et al. | .................... | 702/27 |
| 6,081,766 A * | 6/2000 | Chapman et al. | ................ | 702/27 |
| 6,185,506 B1 * | 2/2001 | Cramer et al. | ..................... | 506/8 |
| 6,240,374 B1 * | 5/2001 | Cramer et al. | ..................... | 506/8 |

(Continued)

FOREIGN PATENT DOCUMENTS

JP 2001-067495 3/2001

OTHER PUBLICATIONS

Bajaj, Chandrajit. "Modeling and Visualization for Dynamic Molecular Stucutres", Nov. 2002.*

(Continued)

*Primary Examiner* — Shambhavi Patel
(74) *Attorney, Agent, or Firm* — IPUSA, PLLC

(57) ABSTRACT

A molecular simulation method that acquires physical properties or physical quantities of a predetermined shape using simulation, including arranging atoms in the predetermined shape, acquiring interatomic potential based on positions of the arranged atoms, and carrying out a molecular dynamics calculation based on the acquired interatomic potential, and acquiring the physical properties or the physical quantities.

9 Claims, 13 Drawing Sheets

U.S. PATENT DOCUMENTS

| | | | |
|---|---|---|---|
| 6,421,612 B1* | 7/2002 | Agrafiotis et al. | 702/19 |
| 6,453,246 B1* | 9/2002 | Agrafiotis et al. | 702/27 |
| 6,490,588 B2* | 12/2002 | Itai et al. | 707/770 |
| 6,782,323 B2* | 8/2004 | Kotani | 702/27 |
| 7,110,888 B1* | 9/2006 | Nicholls | 702/27 |
| 7,165,017 B2* | 1/2007 | Paterson et al. | 703/22 |
| 7,188,055 B2* | 3/2007 | Agrafiotis et al. | 703/2 |
| 7,305,331 B2* | 12/2007 | Allen et al. | 703/11 |
| 7,603,326 B2* | 10/2009 | Bonabeau et al. | 706/13 |
| 7,650,265 B2* | 1/2010 | Taylor et al. | 703/6 |
| 7,679,615 B2* | 3/2010 | Kim et al. | 345/418 |
| 2009/0006059 A1* | 1/2009 | Arora et al. | 703/11 |

OTHER PUBLICATIONS

Tabar, et al. "Interatomic Potential Models for Nanostructures", American Scientific Publishers, 2003.*

Kido et al. "Molecular Dynamics Simulator Workbench: COMDES", 1990.*

Belytschko et al. "Atomistic Simulations of Nanotube Fracture", 2002.*

Jiang et al. "A Comparison of Different Interatomic Potentials: Radius Effect of Single Wall Carbon Nanotubes", IUTAM Symposium on Mechanical Behavior and Micro-Mechanics of Nanostructured Materials, 121-134. © 2007 Springer.*

Dudarev et al. "A 'magnetic' interatomic potential for molecular dynamics simulations", J. Phys.: Condens. Matter 17 (2005) 7097-7118.*

Poupon, Anne. "Voronoi and Voronoi-related tessellations in studies of protein structure and interaction", Current Opinion in Structural Biology 2004, 14:233-241.*

Gao, Guanghua. "Large Scale Molecular Simulations with Application to Polymers and Nano-scale Materials", 1998.*

Ogata et al. "Hybrid finite-element/molecular-dynamics/electronic-density-functional approach to materials simulations on parallel computers", Computer Physics Communications 138 (2001) 143-154.*

Ware, Will. "Distributed Molecular Modeling over Very-Low-Bandwidth Computer Networks", 1997.*

Akihiro Nakatani, "Shuju no Kaiso ni Okeru Sosei Riron no Hatten : 7. Bunshi Dorikigakuho ni yoru Sosei Henkei no Simulation", Journal of the Society of Materials Soecience, Japan, Nov. 15, 1999, vol. 48, No. 11, pp. 1328 to 1334.

Masanori Kayama, Nano Simulation Gijutsu Handbook, 1st edition, Kyoritsu Shuppan Co., Ltd., Jul. 15, 2006, pp. 244 to 245, 294 to 295, 306 to 308.

Toshihiro Kido, "Bunshi Dorikigaku Simulator no Tameno Workbench : COMDES I", Preprints of the 13th Symposium on Chemical Information and Computer Science and the 18th Symposium on Structure-Activity Relationships, Nov. 28-30, Nov. 19, 1990, pp. 113 to 116.

Fujitsu S Family MASPHC/WB Shiyo Tebikisho (Keisan Zairyo Sekkei System/Wokbench), 1st edition, Fujitsu Ltd., Oct. 31, 1994, pp. 72 to 75, 81 to 95, 103 to 111.

Isao Okada and Eiji Ohsawa, "Introduction to Molecular Dynamics", Dec. 6, 1989, Kaibundo.

"Fujitsu MASPHYC/MD Guidebook (Computational Material Design System)" by Fujitsu Limited, 1997, First Version, pp. 1, 18-20, 25-26.

* cited by examiner

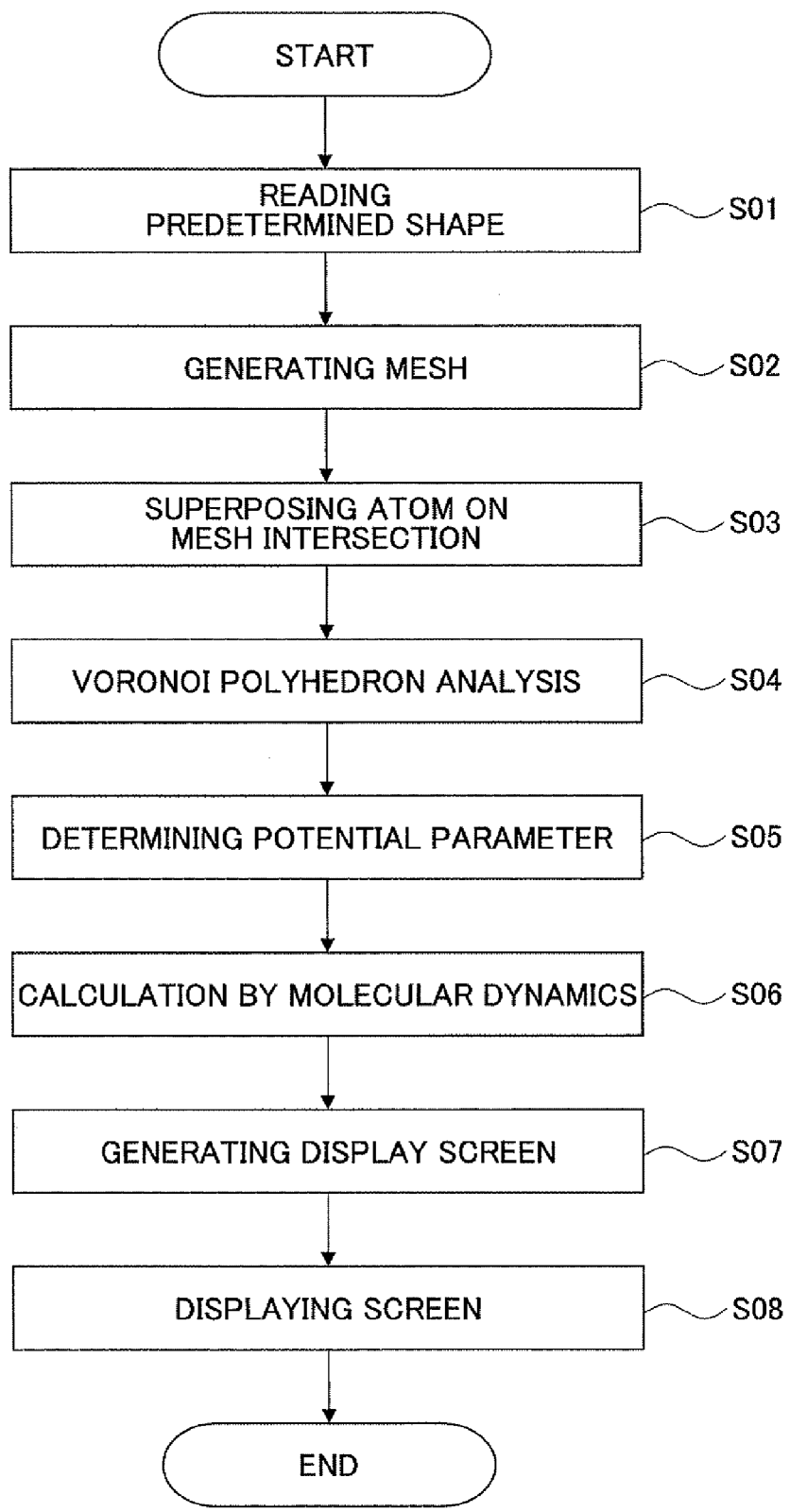

LOAD OF 100[N]

YOUNG'S MODULUS : 208[GPa]
DENSITY : 7800[kg/m³]
WIDTH × HEIGHT × DEPTH
= 10 × 100 × 1[mm]

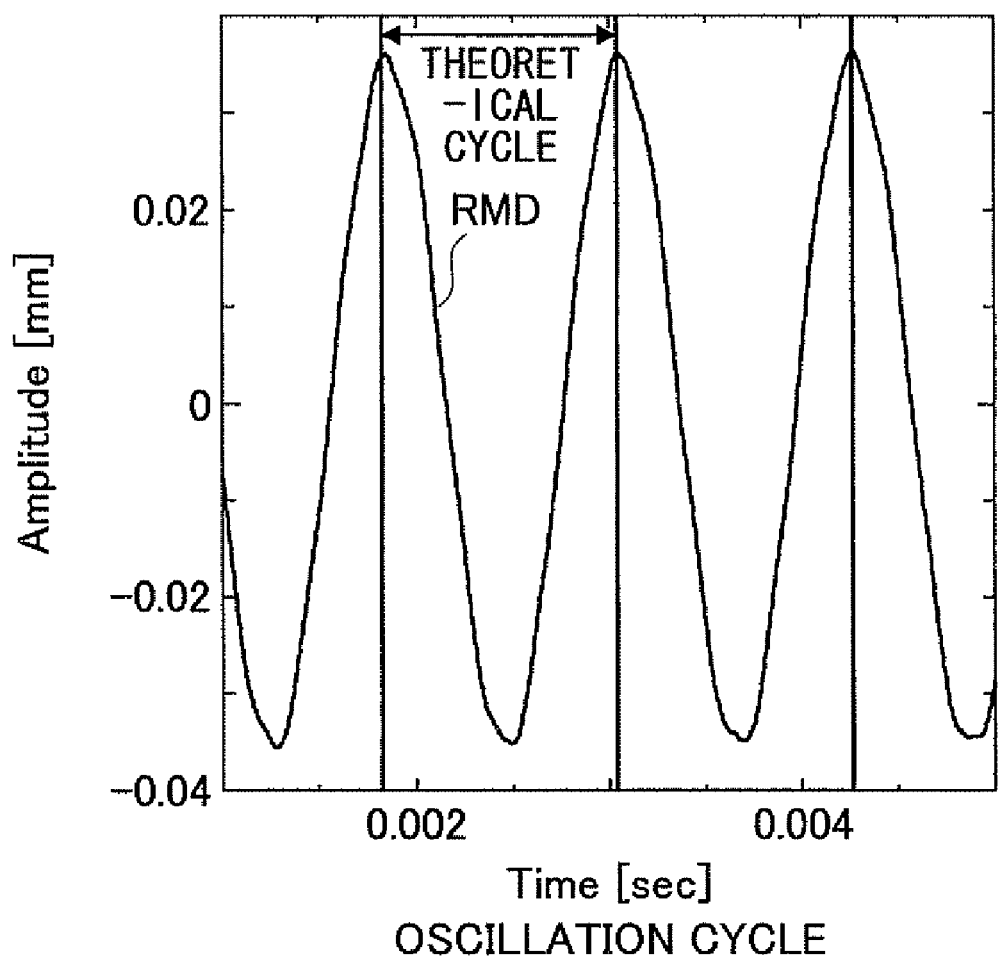

MOLECULAR SIMULATING METHOD, MOLECULAR SIMULATION DEVICE, MOLECULAR SIMULATION PROGRAM, AND RECORDING MEDIUM STORING THE SAME

TECHNICAL FIELD

The present invention relates to a molecular simulation method, a molecular simulation device, a molecular simulation program, and a recording medium storing the molecular simulation program. More particularly, the present invention relates to a molecular simulation method, a molecular simulation device, a molecular simulation program, and a recording medium storing the molecular simulation program, which enable stably and properly acquiring the physical properties or physical quantities.

BACKGROUND ART

Conventionally, there is known molecular simulation based on a molecular dynamics method as a methodology of pursuing a phenomenon of entire quantum mechanics using computing machines on the basis of classical dynamics, quantum mechanics or the like. Molecular simulation enables elucidating at the molecular level physical properties of materials such as molecular potential energy, the most stabilized structure, or the like.

There has been introduced no method of arranging atoms in a complicated structure, an ordinary machine structure or the like because the molecular simulation has mainly been used for presumed physical properties of materials. A finite element method is an example of methods of modeling and calculating the complicated structure after dividing it to finite regions. In the case of two-dimensional calculations, there may be a case where a program for generating a mesh is used in order to thoroughly divide an object with triangle or quadrangular regions (see, for example, Patent Document 1).
[Patent Document 1] Japanese Unexamined Patent Application Publication No. 2001-67495

DISCLOSURE OF THE INVENTION

Problems to be Solved by the Invention

However, when the method of generating the mesh disclosed in Patent Document 1 is applied to, for example, atom arrangement of Molecular Dynamics, there frequently occur cases where the sizes of the triangle regions differ and do not become constant because it is aimed to fill an object region with the triangle regions.

There may be cases where the triangle regions are extremely distorted depending on shapes of arranging atoms. Therefore, when the atoms are simply arranged at grid points of the mesh, an extremely large stress is generated depending on density of an initial atomic geometry. At worst, the calculation of physical quantity may fail.

The present invention is provided in consideration of the above problems. The object of the present invention is to provide a molecular simulation method, a molecular simulation device, a molecular simulation program, and a recording medium storing the molecular simulation program, which enable stably and properly acquiring physical properties or physical quantities.

Means for Solving Problems

Accordingly, one aspect of the present invention may be to provide a molecular simulation method that acquires physical properties or physical quantities of a predetermined shape using simulation including arranging atoms in the predetermined shape, acquiring interatomic potential based on positions of the arranged atoms, and carrying out a molecular dynamics calculation based on the acquired interatomic potential and acquiring the physical properties or physical quantities, solving one or more of the problems discussed above.

This makes it possible to stably and properly acquire the physical properties or physical quantities. Therefore, it becomes possible to realize stabilized calculation without causing a non-physical remaining stress or the like even though a complicated shape is expressed when potential is properly revised using information of the atom arrangement, and reproduction of the physical properties or physical quantities is elaborated.

Further, when the atoms are arranged in the predetermined shape, it is preferable to generate a mesh and arrange atoms on intersections of the generated mesh. This makes it possible to generate the mesh and easily and efficiently arrange the atoms.

Further, it is preferable that the interatomic potential is a pair potential using only a distance between two atoms as an independent variable. This makes it possible to efficiently calculate the pair potential using the easiest form of the potential.

Further, it is preferable that the interatomic potential is acquired based on Voronoi points obtained by a Voronoi polyhedron analysis using the above arranged atom points. It is preferable to include acquiring potential parameters which involve a cross-sectional area on which an atomic force between two atoms acts and an interatomic bond energy, and determining the interatomic potential using the potential parameter. This makes it possible to properly calculate physical properties or physical quantities, and appropriately revise the interatomic potential.

Another aspect of the present invention may be to provide a molecular simulation device that acquires physical properties or physical quantities of a predetermined shape using simulation including an atom arranging part configured to arrange atoms in the predetermined shape, an interatom potential acquiring part configured to acquire interatomic potential based on positions of the atoms arranged by the atom arranging part, and a molecular dynamics calculating part configured to carry out molecular dynamics calculation based on interatomic potential acquired by the interatom potential acquiring part and acquire the physical properties or physical quantities. This makes it possible to stably and properly acquire the physical properties or physical quantities. Therefore, it becomes possible to realize stabilized calculation without causing a non-physical remaining stress or the like even though the complicated shape is expressed when potential is properly revised using information of the atom arrangement, and reproduction of the physical properties or physical quantities is elaborated.

Further, in the above atom arranging part, it is preferable to generate a mesh and arrange atoms on intersections of the generated mesh. This makes it possible to generate the mesh and easily and efficiently arrange the atoms.

Further, it is preferable that the interatomic potential is a pair potential using only a distance between two atoms as an independent variable. This makes it possible to efficiently calculate the pair potential using the easiest form of the potential.

Further, it is preferable the interatomic potential acquiring part acquires potential parameters which involve a cross-sectional area, on which an atomic force between two atoms acts, and an interatomic bond energy, and determines the interatomic potential using the potential parameter. This makes it possible to properly calculate physical properties or physical quantities, and appropriately revise the interatomic potential.

Another aspect of the present invention may be to provide a molecular simulation program that acquires physical properties or physical quantities of a predetermined shape using simulation embodied in a computer-readable medium and representing a sequence of instructions, which when executed by a computer, the instructions cause the computer to function as an atom arranging part configured to arrange atoms in the predetermined shape, an interatom potential acquiring part configured to acquire interatomic potential based on positions of the atoms arranged by the atom arranging part, and a molecular dynamics calculating part configured to carry out a molecular dynamics calculation based on interatomic potential acquired by the interatom potential acquiring part and acquiring the physical properties or physical quantities. This makes it possible to stably and properly acquire the physical properties or physical quantities. Therefore, it becomes possible to realize stabilized calculation without causing a nonphysical remaining stress or the like even though a complicated shape is expressed when potential is properly revised using information of the atom arrangement, and reproduction of the physical properties or physical quantities is elaborated. It is possible to realize a molecular simulating process by installing an executable program on the computer.

Further, it is preferable that the above atom arranging part generates a mesh in the shape and arranges atoms on intersections of the generated mesh. This makes it possible to generate the mesh and easily and efficiently arrange the atoms.

Further, it is preferable that the interatomic potential is a pair potential using only a distance between two atoms as an independent variable. This makes it possible to efficiently calculate the pair potential using the easiest form of the potential.

Further, it is preferable that the interatomic potential acquiring part acquires potential parameters which involve a cross-sectional area on which an atomic force between two atoms acts and an interatomic bond energy, and determines the interatomic potential using the potential parameters. This makes it possible to properly calculate physical properties or physical quantities, and appropriately revise the interatomic potential.

Further, the present invention provides a computer readable recording medium which stores the above molecular simulation program. The computer readable recording medium makes it possible to easily install the molecular simulation program on plural computers.

Effect of the Invention

According to the present invention, it is possible to stably and properly acquire the physical properties or physical quantities. This makes it possible to realize stabilized calculations without causing a non-physical remaining stress or the like even though a complicated shape is expressed when potential is properly revised using information of the atom arrangement, and reproduction of the physical properties or physical quantities is elaborated.

BRIEF DESCRIPTION OF DRAWINGS

FIG. 3 An example of a molecular simulation procedure of the embodiment.

FIG. 7C An example of a graph illustrating a relationship between an oscillation cycle (Time) of a beam and the amplitude (Amplitude) of the oscillation cycle.

EXPLANATION OF REFERENCE SYMBOLS

Figure 1:
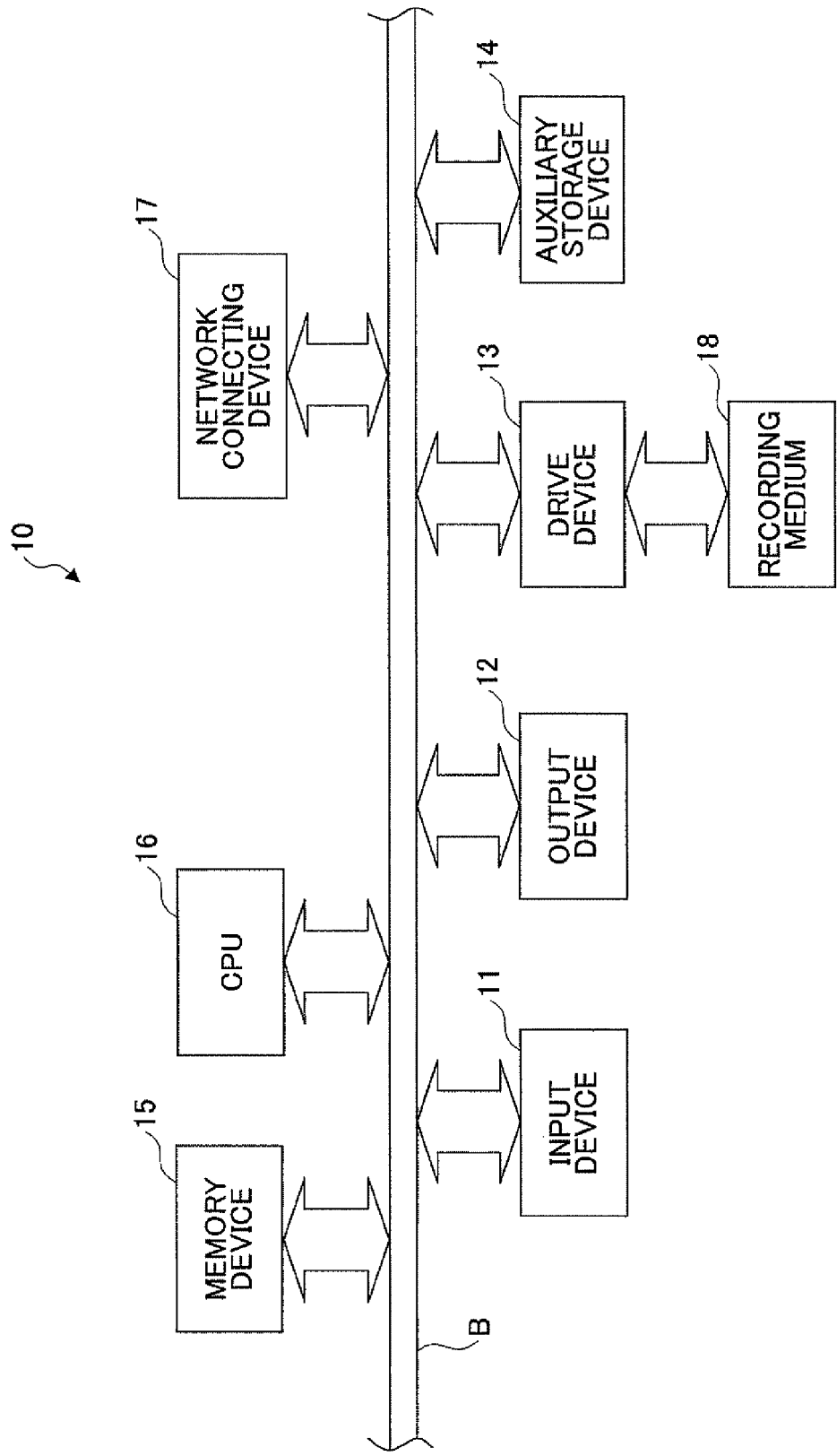
FIG. 1 An example of a hardware structure of a molecular simulation device of the embodiment.

10: molecular simulation device
11: input device
12: output device
13: drive device
14: auxiliary storage device
15: memory device
16: CPU
17: network connecting device
18: recording medium
21: input part
22: output part
23: accumulating part
24: atom arranging part
25: interatomic potential acquiring part
26: molecular dynamics calculation part
27: screen generating part
28: sending and receiving part
29: controlling part
31: complicated shape
32, 41, 51: atom
42, 52: line segment
43: bisector
53: perpendicular

BEST MODE FOR CARRYING OUT THE INVENTION

Summary of the Present Invention

The present invention provides a method of properly revising potential using information of peripheral atoms while maintaining an atom arrangement when atoms are arranged in a complicated shape using, for example, a general-purpose mesh generation software or the like. A calculation method for revising the potential may be a molecular dynamics method, for example. However, the present invention is not limited thereto, and the calculation method may be a method of searching for a stabilized point of the potential such as a Monte Carlo method.

In the molecular dynamics method (MD method), a Newtonian equation in classical dynamics is solved under interatomic potential between two or more atoms, and a static or dynamic stabilized structure or a dynamic process (dynamics) is analyzed. It is possible to calculate with molecular dynamics an ensemble, i.e. a statistical mass, such as a constant temperature, a constant pressure, a constant energy, a constant volume and a constant chemical potential. Further, it is possible to add various restraint conditions like a bond length and a fixation of position to the calculation.

Modes of preferably carrying out the molecular simulation method, the molecular simulation device, the molecular simulation program, and the recording medium storing the molecular simulation program according to the present invention having the above-mentioned features are described in detail in reference to figures.

(Device Structure of the Present Embodiment)

First, the molecular simulation device of the present embodiment is described in reference to the figures. FIG. 1 illustrates an example of a hardware structure of a molecular simulation device of the present embodiment.

The molecular simulation device 10 includes an input device 11, an output device 12, a drive device 13, an auxiliary storage device 14, a memory device 15, a central processing unit 16, and a network connecting device 17, mutually connected by a system bus B.

The input device 11 includes a pointing device operated by a user or the like such as a keyboard and a mouse. Input to the input device 11 are various signals from the user or the like such as Instructions of executing programs and displaying results of processes, and input of data necessary for the processes. The output device 12 includes a display for displaying various windows, data or the like necessary for operating a computer which carries out processes of the present invention. It is possible to display execution transit, results, or the like of the program with a control program installed in the CPU 16.

In the present invention, an executable program installed on the computer may be provided by the recording medium 18 such as a CD-ROM. The recording medium 18 having the executable program recorded on it may be mounted on the drive device 13. The executable program included in the recording medium 18 is installed on auxiliary storage device 14 via the driving device 13 from the drive device 13.

The auxiliary storage device 14 is a part configured to store data such as a hard disk. The executable program of the present invention, the control program provided to the computer, input data necessary for the molecular simulation of the present invention, results of processes of the molecular simulation of the present invention, and so on are stored in the auxiliary storage device 14. Further, when necessary, the input data and results of processes are input to and output from the auxiliary storage device 14.

The memory device 15 stores the executable program read out of the auxiliary storage device 14 by the CPU 16. The memory device 15 includes a Read Only Memory (ROM), a Random Access Memory (RAM) or the like.

The CPU 16 may realize various processes by controlling an entire process of the computer such as various calculations and data inputs and data outputs to and from various hardware components based on the control program such as an Operating System (OS), the executable program, which is read out and stored by the memory device 15, or the like. Further, the CPU 16 may obtain various necessary information during the execution of the program from the auxiliary storage device 14. The results of processes or the like may be stored in the auxiliary storage device 14.

When the network connecting device 17 is connected to a communication network or the like, the network connecting device 17 may obtain the executable program from another terminal connected to a communication network, or provide execution results obtained by carrying out the executable program or the executable program itself of the present invention to another terminal or the like.

(Molecular Simulating Device: Example of Functional Configuration)

Figure 2:
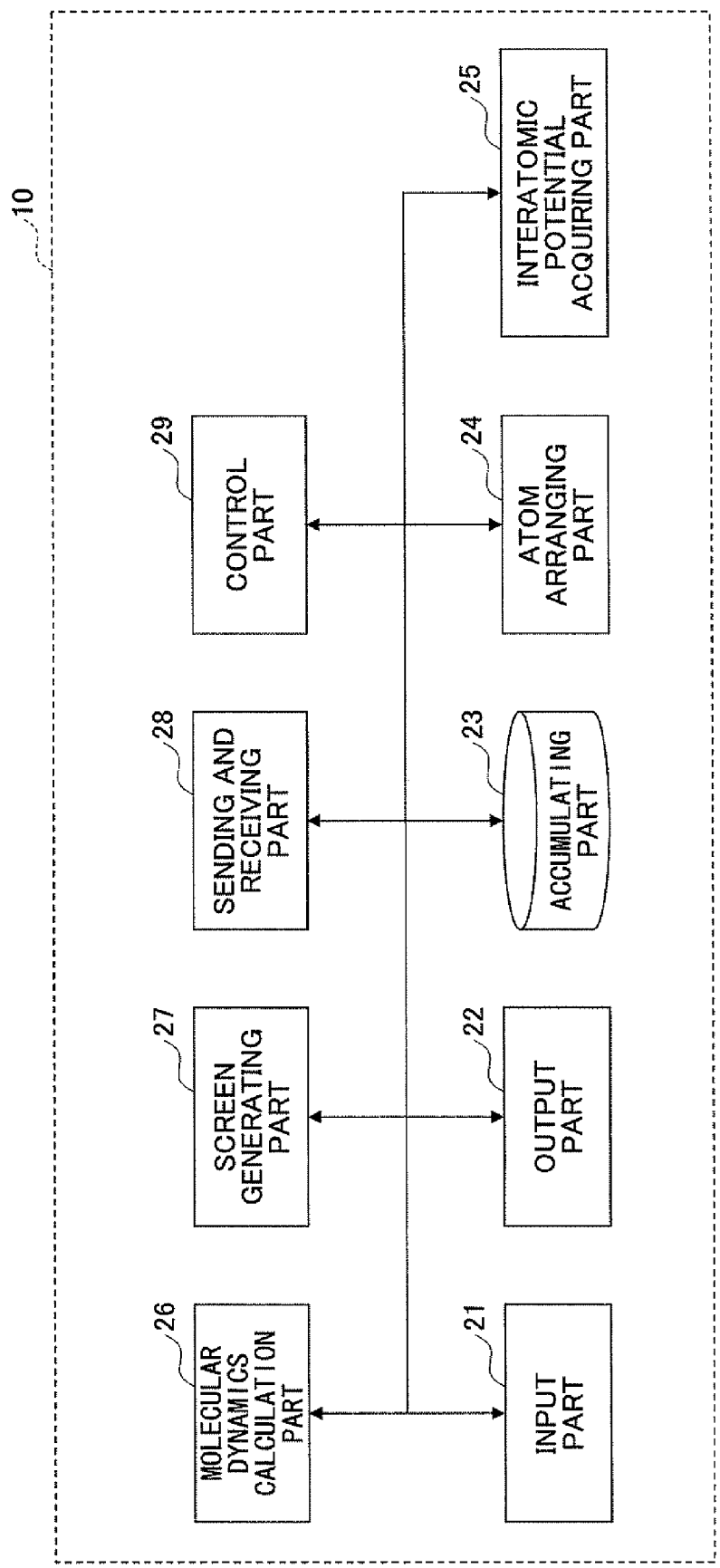
FIG. 2 An example of a functional configuration of a molecular simulation device.

Next, a functional configuration of the molecular simulation device 10 is described in reference to figures. FIG. 2 illustrates an example of the functional configuration of the molecular simulation device. The molecular simulation device 10 includes an input part 21, an output part 22, an accumulating part 23, an atom arranging part 24, an interatomic potential acquiring part 25, a molecular dynamics calculation part 26, a screen generating part 27, a sending and receiving part 28, and a controlling part 29.

The input part 21 receives an input of various instruction information pieces accompanied in carrying out the molecular simulation from a user or the like. The input part 21 includes a keyboard, a pointing device like a mouse, an audio input interface like a microphone, or the like.

Further, the output part 22 displays the content of the instruction input by the input part 21, a content and result of compilation provided to the molecular simulation generated based on the content of the instruction, a screen for instructing execution of the executable program, and contents of transit of interatomic potential parameters. The output part 22 includes a display, a speaker or the like.

Further, the accumulating part 23 accumulates the result of the atom arrangement after the molecular simulation is carried out, the result of arranging the interatomic potential, the input data and so on. The accumulating part 23 may obtain the input data or the like from an external device (not illustrated) connected via the sending and receiving part 28 and the communication network or the like, and accumulates the obtained input data.

The atom arranging part 24 arranges atoms in, for example, a predetermined shape (a simple shape and a complicated shape). In order to arrange the atoms at proper positions, many meshes are generated on the predetermined shape to allocate the atoms to grid points of the meshes, or atoms are generated inside the predetermined shape to fill the predetermined shape with the atoms after superposing the atoms at the frame of the predetermined shape.

Therefore, when the above method of generating the meshes is used, the atom arranging part 24 specifically arranges the atoms at mesh intersections obtained by generating the meshes, for example.

The interatomic potential acquiring part 25 properly revises the potential using information of surrounding atoms while maintaining the atoms arranged by the atom arranging part 24 as is. Specifically, the atoms arranged by generating the meshes undergo a Voronoi polyhedron analysis to thereby determine potential parameters.

The molecular dynamics calculation part 26 calculates physical properties or physical quantities based on the potential parameters obtained from the interatomic potential acquiring part 25.

The screen generating unit 27 displays an appearance of the atoms arranged in the predetermined shape by the atom arranging part 24, initial setting or execution results in the interatomic potential acquiring part 25, physical properties calculated by the molecular dynamics calculation part 26, and results of processes such as tables, graphs, charts or the like corresponding to the physical properties.

The sending and receiving part 28 is a communication interface which acquires necessary data from the external devices connected via the communication network like the Internet, and sends results of the molecular simulation of the present invention.

The controlling part 29 controls the entire functional configurations of the molecular simulation device 10. Specifically, the controlling part 29 controls processes such that the atom arranging part 24 arranges the atoms based on the input information input from the user by the input part 21, the interatomic potential acquiring part 25 obtains the potential parameters, and the molecular dynamics calculation part 26 obtains the physical properties.

This makes it possible to properly arrange the atoms in the complicated shape using molecular dynamics. Further, this makes it possible to stably and properly acquire the physical properties or physical quantities. Therefore, when the complicated shape is calculated by a molecular dynamics method, the interatomic potential may be revised by stably calculating an insufficient atom arrangement and properly acquiring the physical properties or physical quantities.

(Example of Molecular Simulation Procedure)

Next, the molecular simulation procedure by the executable program (molecular simulation program) of the present invention is described. FIG. 3 illustrates an example of the molecular simulation procedure of the embodiment.

As illustrated in FIG. 3, when the atoms are arranged in the predetermined shape such as a complicated shape, the predetermined shape is first read from data of Computer Aided Design (CAD) in step S01, and meshes are generated in step S02. The meshes may be generated by, for example, the method of generating mesh described in Patent Document 1.

The method of generating mesh is, for example, a triangulation division based on a Voronoi Tessellation, a transfinite mapping method of expanding a mapping region from a quadrangle to another shape, a boundary fit method of solving an elliptic partial differential equation, an advancing front type method of generating a triangle (a tetrahedron) from a certain border, a quadtree representation method, an oct-tree representation method, a paving method of arranging quadrangular meshes sequentially from a border and revising when contradiction occurs, a hexahedron mesh generation method (whisker weaving method) of generating hexahedron meshes from surface quadrangulation division data toward the inside, a Grid Based method of arranging cubic grids inside a three-dimensional figure and processing a surface of the three-dimensional figure, and a space division method of dividing into basic regions with mapping using medial surfaces to generate hexahedrons, where the number of ridge lines is three in all apexes, an adaptive method of presuming distribution of discrete errors based on an analysis result and improving meshes so as to decrease errors, or the like.

It is possible to use general-purpose computer aided engineering (CAE) software such as "PATRAN", "FEMAP", "ATLAS", "MENTAT", "TRUEGRID", and "SOLID-WORKS", for example.

Then, atoms are superposed on the mesh intersections in step S03. The atoms undergo a Voronoi polyhedron analysis in step S04.

Specifically, a Voronoi diagram including Voronoi-divided regions is acquired by dividing a set of points representing the atoms. The Voronoi-divided regions are determined by a part of the set of points having the same distance which is shortest from one reference point (i.e., kernel point, described later) among the set of points. The Voronoi-divided regions are visualized by connecting the part of the set of points with lines. The part of the set of points are referred to as "Voronoi points".

Interatomic potential parameters are determined in the process of step S04. In the process of step S05, parameters such as an interatomic distance "$r_0$" at which a structure of the atoms is most stabilized and a bond energy "$\epsilon$" are determined based on a Young's modulus predetermined by a user.

Further, in step S06, the physical properties or physical quantities in molecular dynamics are calculated based on an interatomic potential parameter obtained in step S05. In step S07, there is generated a screen of displaying a processing result or the like obtained in the process of step S06 on an output unit 12 or an output part 22. Then, the generated screen is displayed in step S08.

(Processes of Steps S04 Thru S06)

Next, the processes carried out in step S04 of Voronori polyhedron analysis thru step S06 of calculation by molecular dynamics are specifically described.

First, the Voronoi polyhedron is described. For example, Formula 1 defines power relationships $V_i$ of $p_i$ when n points $p_1, p_2, \ldots, p_n$ are given on a plane surface $R^2$.

[Formula 1]

$$V_i = \{x \in R^2 | d(x, p_i) \leq d(x, p_j), j \neq i, j = 1, \ldots, n\} \qquad (1)$$

In this case, a range where x may cover is referred to as a Voronori-divided region. Point $p_i$ is the kernel point of the Voronori-divided region (i.e. an atom position in the embodiment). The Volonori-divided region becomes a convex polyhedron. The convex polyhedron is called "Voronoi polyhedron". In step S04, the Voronoi polyhedron is used for analysis. An example of measures of the analysis is specifically described later.

Next, the concept of a molecular dynamics method is described. A motion equation which should be actually solved is the Newton's equation of motion of Formula 2, described below. Formula 2 is solved by directly integrating numbers.

[Formula 2]

$$m_i \frac{d^2 r_i}{d t_2} = F_i \qquad (2)$$

In Formula 2, $m_i$ designates an atomic mass, $r_i$ designates a position vector, and $F_i$ designates a vector acting on an atom i (resultant force of interatomic interaction). Further, velocity $v_i$ can be expressed by Formula 3 as follows.

[Formula 3]

$$m_i \frac{d v_i}{d t} = F_i \qquad (3)$$

Therefore, when a time count is represented by $\Delta t$, the velocity $v_i$ is obtainable from Formula 4 as follows.

[Formula 4]

$$m_i \frac{v_i(t+\Delta t/2) - v_i(t-\Delta t/2)}{\Delta t} = F_i \qquad (4)$$

$$\therefore v_i(t+\Delta t/2) = v_i(t-\Delta t/2) + \Delta t \frac{F_i}{m_i}$$

Further, the position $r_i$ of the atom i can be obtained by Formula 5 as follows.

[Formula 5]

$$r_i(t+\Delta t) = r_i(t) + \Delta t v_i(t+\Delta t/2) \qquad (5)$$

When an initial position and an initial velocity are predetermined, it is possible to sequentially renew the positions and velocities of the atoms using Formula 4 and Formula 5.

The numeric integration method is called a "leapfrogging method", which is described in Okada Isamu, Introduction to molecular simulation, page 47, Kaibun-dou, 1989.

A force F1 acting on the atom is obtainable from Formula 6 as follows.

[Formula 6]

$$F_i = -\sum_{i<j}^{N} \nabla \phi(r_{ij}) \qquad (6)$$

Reference symbol φ designates interatomic potential, and reference symbol N designates the total number of atoms. In order to obtain the velocities and the positions of the atoms, it is sufficient to acquire only atomic force. In order to obtain the interatomic force, it is sufficient to determine the interatomic potential.

Therefore, it is possible to carry out calculation of molecular dynamics by determining only the interatomic potential. However, the determination of the potential largely depends on experience of a person who carries out the calculation of molecular dynamics. There may be many cases where the calculation of molecular dynamics is not easy. Therefore, the potential may be determined in conformity with the arrangement of the peripheral atoms, and the physical properties of the material may be reproduced in the present invention.

In the embodiment, the potential determined using only a distance between two atoms as an independent variable is referred to as a pair potential, which is the simplest potential type. When the pair potential is expressed by an equation, it can ordinarily be expressed by Formula 7.

[Formula 7]

$$\phi(r_{ij}) = \varepsilon f\left(\frac{r_{ij} - r_0}{\sigma}\right) \qquad (7)$$

Reference symbol "ε" designates a potential parameter of a bond energy. Reference symbol "σ" designates the size of the atom. Reference symbol "$r_0$" designates the most stabilized interatomic distance. Reference symbol "$r_{ij}$" designates an actual interatomic distance.

When the potential is used to express a complicated shape while maintaining a face-centered cubic lattice (the crystal structure having the smallest total bond energy or the like of the atoms or the like in the crystal structure), there is a need of revising the potential because of the following problems.

Figure 4A:
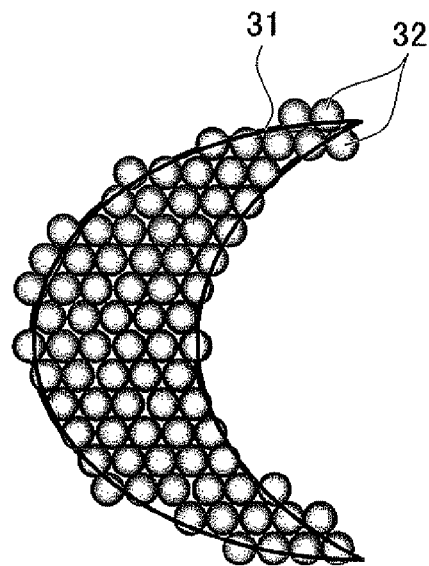
FIG. 4A An example of explaining a reason for revising potential when a complicated shape is expressed.
Figure 4B:
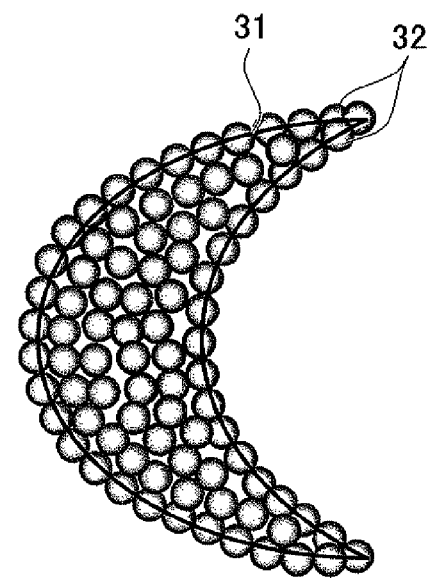
FIG. 4B An example of explaining the reason for revising potential when the complicated shape is expressed.

FIG. 4A and FIG. 4B illustrate examples of explaining reasons for revising potential when a complicated shape is expressed.

When the atoms 32 are arranged on the complicated shape 31 while maintaining the face-centered cubic lattice using the above potential, the surface of the complicated shape 31 inevitably becomes uneven as illustrated in FIG. 4A. Further, as illustrated in FIG. 4B, when the atoms 32 are first superposed on the periphery of the complicated shape 31, and thereafter the atoms 32 are filled inside the complicated shape 31, it becomes possible to definitely express a smooth surface. However, a remaining stress and spaces are generated under the state. Therefore, the energy is not stabilized. Then, it is necessary to revise the potential in conformity with the arrangement of the arranged peripheral atoms.

In the embodiment, the parameters are derived based on Young's modulus. The following example describes application of a revising method using Lennard-Jones potential as a typical pair potential. The potential may be expressed by Formula 8 as follows.

[Formula 8]

$$\phi(r_{ij}) = 4\varepsilon\left[\left(\frac{\sigma}{r_{ij}}\right)^{12} - \left(\frac{\sigma}{r_{ij}}\right)^{6}\right] \qquad (8)$$

Next, Taylor expansion is applied to Formula 8 to the terms up to the second order at $r=r_0$. Then, the potential expressing an elastic region may be expressed like Formula 9 as follows.

[Formula 9]

$$\phi(r_{ij}) = \phi^{(1)}(r_0)(r_{ij}-r_0) + \tfrac{1}{2}\phi^{(2)}(r_0)(r_{ij}-r_0)^2 \qquad (9)$$

In Formula 9, reference symbol $\phi^{(1)}$ designates φ applied with one-time differentiation, and reference symbol $\phi^{(2)}$ designates φ applied with two-times differentiation. Further, reference symbol $r_0$ designates the most stabilized interatomic distance. The most stabilized interatomic distance $r_0$ may be expressed by Formula 10 using Lennard-Jones potential as follows.

[Formula 10]

$$r_0 = 2^{1/6}\sigma \qquad (10)$$

Figure 5:
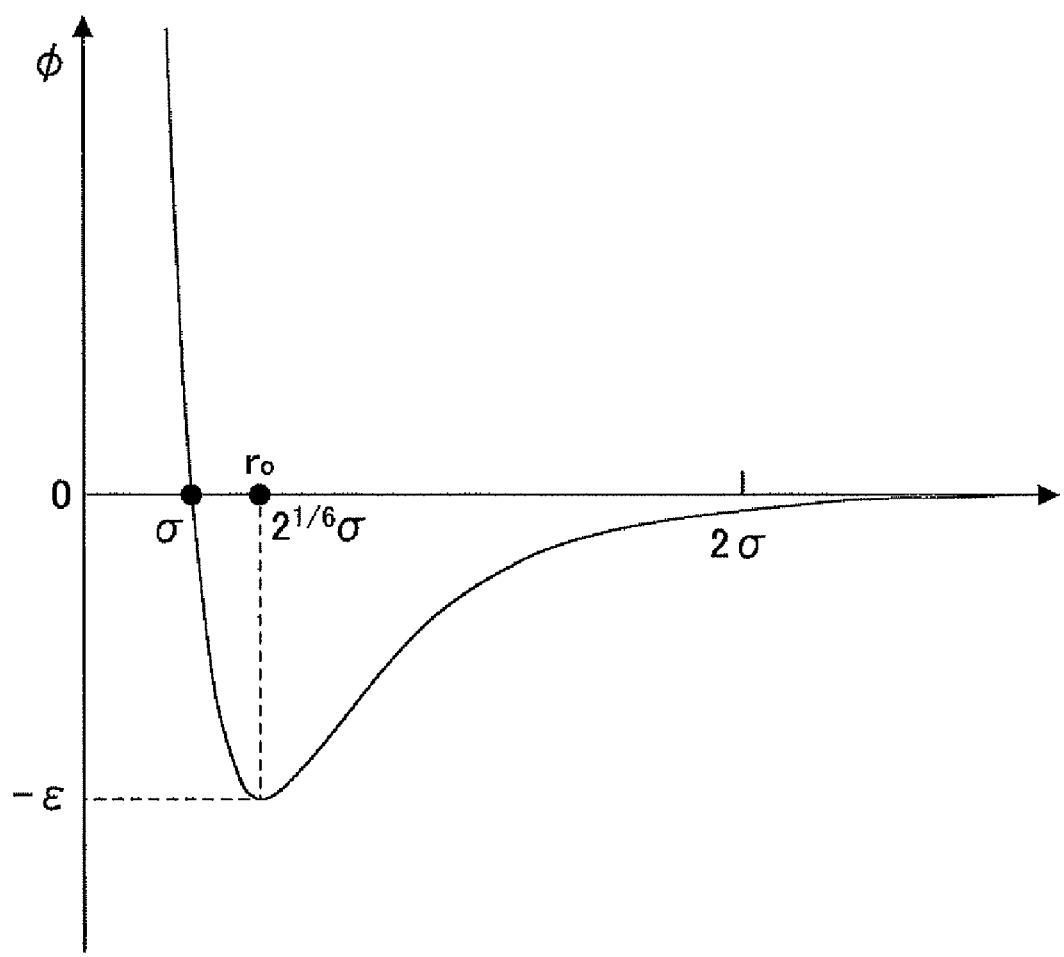
FIG. 5 An example of Lennard-Jones potential.

FIG. 5 illustrates an example of Lennard-Jones potential. In FIG. 5, the axis of abscissa represents the interatomic distance (r), and the axis of ordinate represents the interatomic potential (φ). As illustrated in FIG. 5, the interatomic potential has the minimum value –ε in case of $r=r_0$.

Further, since $\phi^{(1)}$ and $\phi^{(1)}$ are expressed by Formula 11 and Formula 12 as follows, Formula 13 may be expressed as follows by using Formula 10 described above.

[Formula 11]

$$\phi^{(1)}(r_{ij}) = \frac{\partial \phi(r_{ij})}{\partial r_{ij}} = -\frac{24\varepsilon}{r_{ij}}\left[2\left(\frac{\sigma}{r_{ij}}\right)^{12} - \left(\frac{\sigma}{r_{ij}}\right)^{6}\right] \qquad (11)$$

$$\phi^{(2)}(r_{ij}) = \frac{\partial\left\{\frac{\partial \phi(r_{ij})}{\partial r_{ij}}\right\}}{\partial r_{ij}} = \frac{24\varepsilon}{r_{ij}^2}\left[26\left(\frac{\sigma}{r_{ij}}\right)^{12} - 7\left(\frac{\sigma}{r_{ij}}\right)^{6}\right] \qquad (12)$$

[Formula 12]

$$\left(\frac{\sigma}{r_0}\right)^{12} = \frac{1}{4}, \left(\frac{\sigma}{r_0}\right)^6 = \frac{1}{2} \quad (13)$$

Therefore, a shape of harmonic oscillator potential is obtainable as illustrated in Formula 14 by substituting Formula 9 with Formula 11, Formula 12, and Formula 13.

[Formula 13]

$$\phi(r_{ij}) = -\frac{24\varepsilon}{r_0}\left[2\frac{1}{4} - \frac{1}{2}\right](r_{ij} - r_0) + \frac{1}{2}\frac{24\varepsilon}{r_0^2}\left[26\frac{1}{4} - 7\frac{1}{2}\right](r_{ij} - r_0)^2 \quad (14)$$

$$= \frac{36\varepsilon}{r_0^2}(r_{ij} - r_0)^2$$

Provided that reference symbol k designates a spring constant, Formula 15 may be derived as follows from Formula 9 described above.

[Formula 14]

$$k = \frac{36\varepsilon}{r_0^2} \quad (15)$$

Further, a relationship between the spring constant and the Young's modulus is expressed by Formula 16 as follows.

[Formula 15]

$$k = \frac{S}{r_0}E \quad (16)$$

Reference symbol S designates a cross-sectional area on which force acts. The bond energy ε is obtained by Formula 17 based on Formula 15 and Formula 16 described above.

[Formula 16]

$$\varepsilon = \frac{r_0}{36}SE \quad (17)$$

Reference symbol $r_0$ designates an interatomic distance in an initial arrangement. In the embodiment, reference symbol $r_0$ designates the most stabilized interatomic distance. It is necessary to independently determine the cross-sectional area S. Specifically, the Voronoi polyhedron analysis may be carried out as described above to determine an area crossing a line segment $r_0$, which represents the interatomic distance, as the cross-sectional area S.

(As to Voronoi Polyhedron Analysis)

Figure 6A:
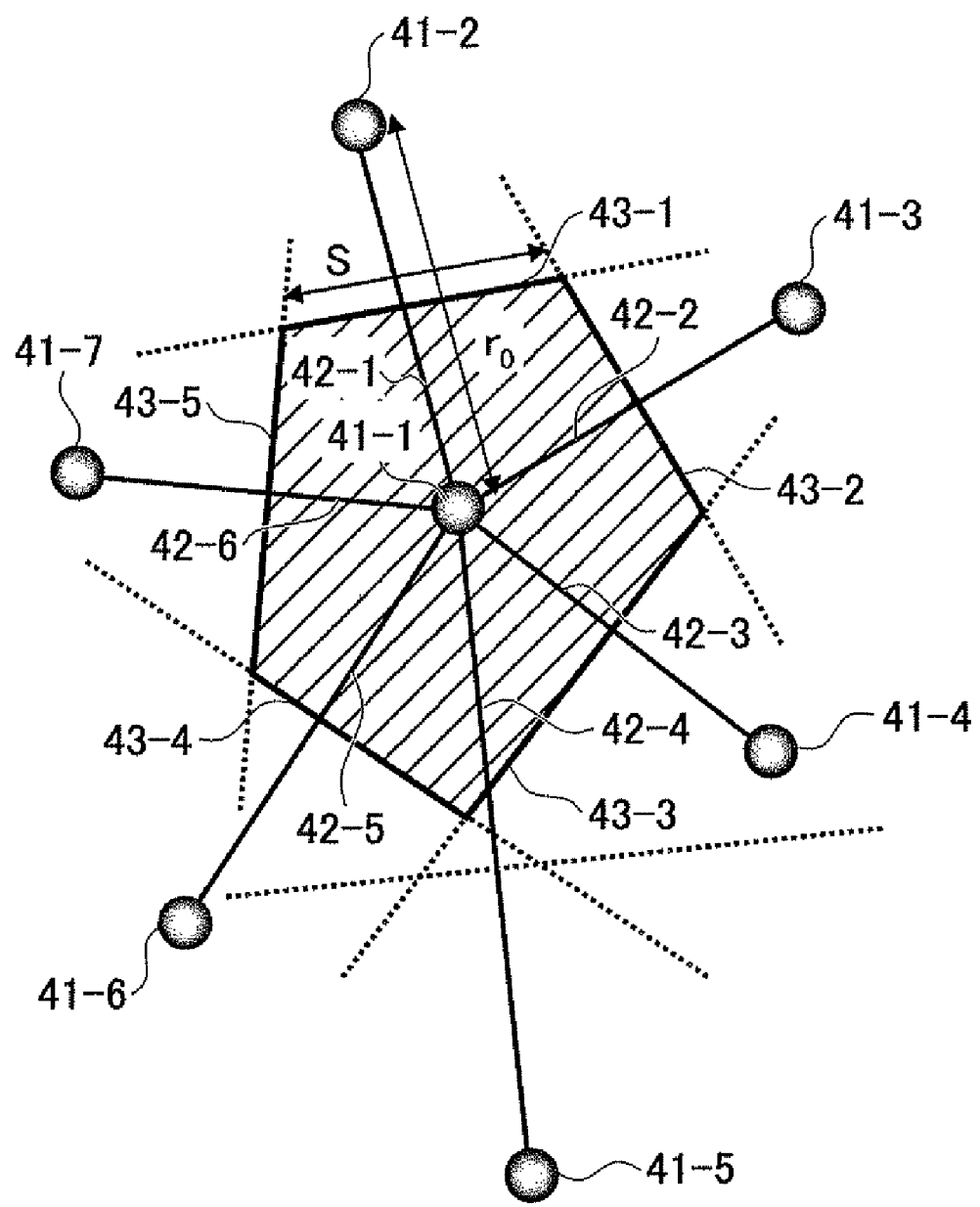
FIG. 6A An example of a Voronoi polyhedron analysis of the embodiment.
Figure 6B:
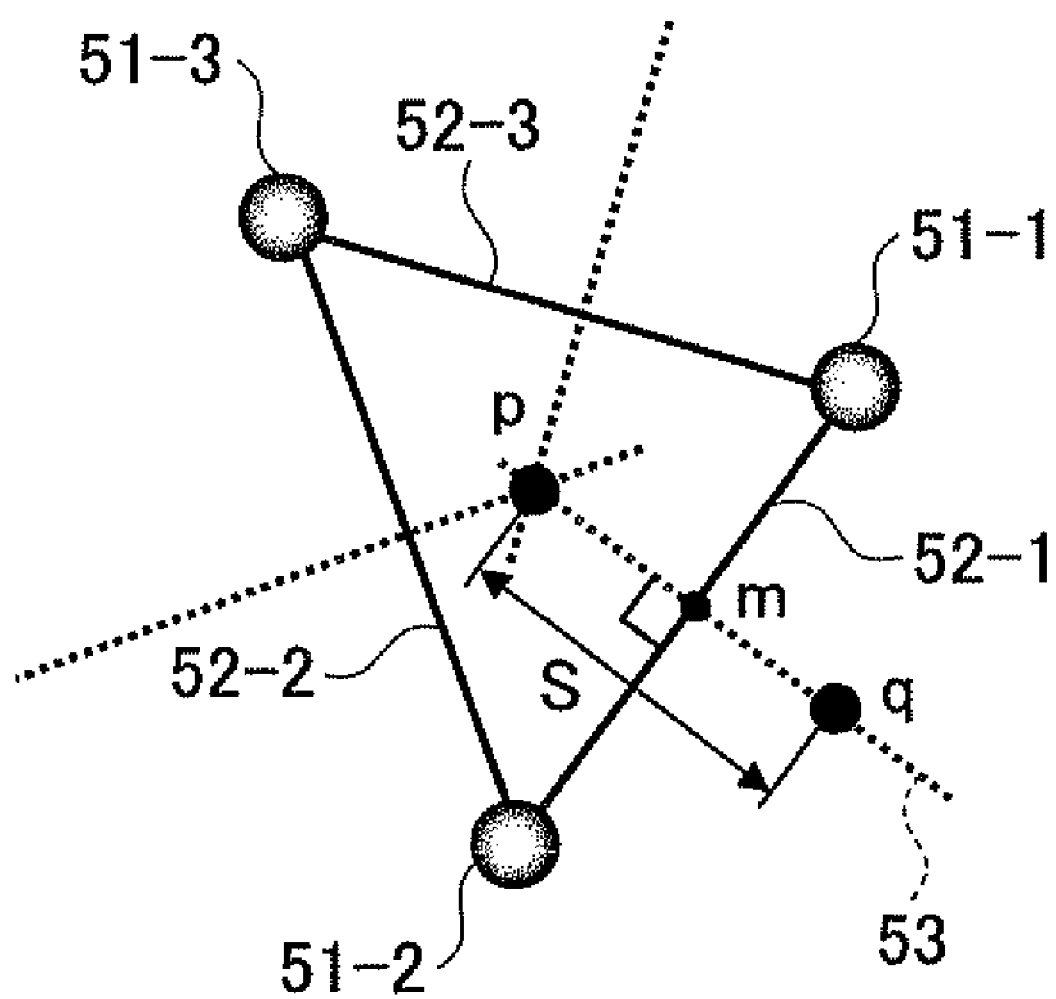
FIG. 6B An example of the Voronoi polyhedron analysis of the embodiment.

The Voronoi polyhedron analysis is specifically described in reference to figures. FIG. 6A and FIG. 6B illustrate examples of the Voronoi polyhedron analysis of the embodiment. In the example of FIG. 6A, atoms 41-1 thru 41-7 surrounding atom 41-1 are illustrated. Particles (atoms) 41-1 thru 41-7 are connected from a kernel point of atom 41-1 by line segments. Further, bisectors (equally dividing surfaces in case of three-dimension) that equally divide line segments 42-1 thru 42-6 obtained as described above in directions perpendicular to the line segments 42-1 thru 42-6. Further, a polygon (a polyhedron in case of three-dimension) surrounded by the bisectors 43-1 thru 43-5 obtained as described above becomes the Voronoi polyhedron. Therefore, it is possible to acquire the area S as described above from the polyhedron as defined above.

It is preferable to apply the above described processes to the all atoms arranged by the atom arranging part 24 or the like. For example, it is not possible to define the above Voronoi polyhedron for atoms existing on a surface side of the shape of an object because the number of the atoms is insufficient.

In the embodiment, the process illustrated in FIG. 6B is applied. Atoms 51-1 and 51-2 (surface atom) among atoms 51-1 thru 51-3 illustrated in FIG. 6B exist on a surface side of the shape of the object. The atom 51-3 (interior atom) exists inside the surface atoms.

Then, a point p is obtained as an intersection of perpendicular bisectors of line segments 52-1, 52-2, and 52-3 connecting the atoms. The point p is one of vertices forming a Voronoi polyhedron. Therefore, the point p is called a Voronoi point.

An intersection between the perpendicular bisector 53 from the Voronoi point p to the line segment 52-1 and the line segment 52-1 is called point m. A point existing on the perpendicular line 53 and apart from the point m by a distance between the points p and m is called point q. It is possible to define an interaction between the atoms 51-1 and 51-2 using an area S defined by the line segments pq based on the points p and q defined as above. The area S is obtained by multiplying the length of the line segment pq by the depth of the line segment pq.

In a three-dimensional case, it is necessary to handle planes instead of line segments. However, the procedure of handling the planes is the same as that of handling the line sections. Therefore, it is possible to determine the interatomic potential parameters without being bothered with intricate determination of the potential parameters by previously using Young's modulus when the simulation is carried out. The above calculation of molecular dynamics is carried out based on the potential parameter. Based on the result of the calculation, physical properties or physical quantities may be determined with high accuracy. Therefore, a macroscopic system may be calculated by applying the above determined potential and the ordinary renormalization theory to the molecular dynamics method.

(Result of Accuracy in Simulation of the Embodiment)

The result of accuracy is explained in reference to the figures. In the following example, the accuracy of the simulation method of the present embodiment is confirmed in an example of a relationship between bending and oscillation of a cantilever beam. The material of the cantilever beam is, for example, SUS steel.

Figure 7A:
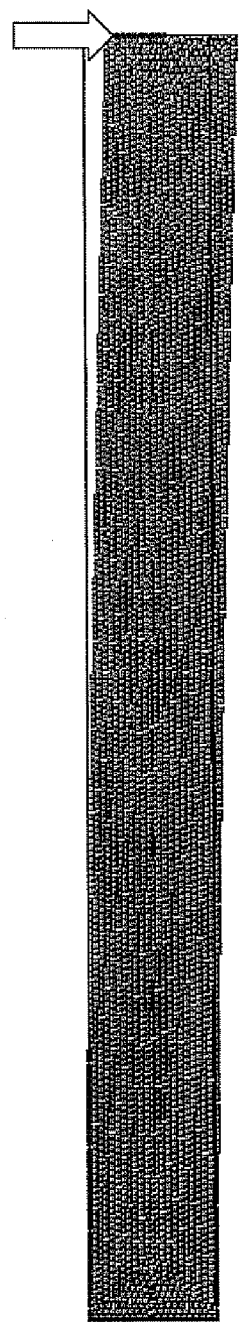
FIG. 7A A beam applied with a load in a lateral direction in a two-dimensional view.
Figure 7B:
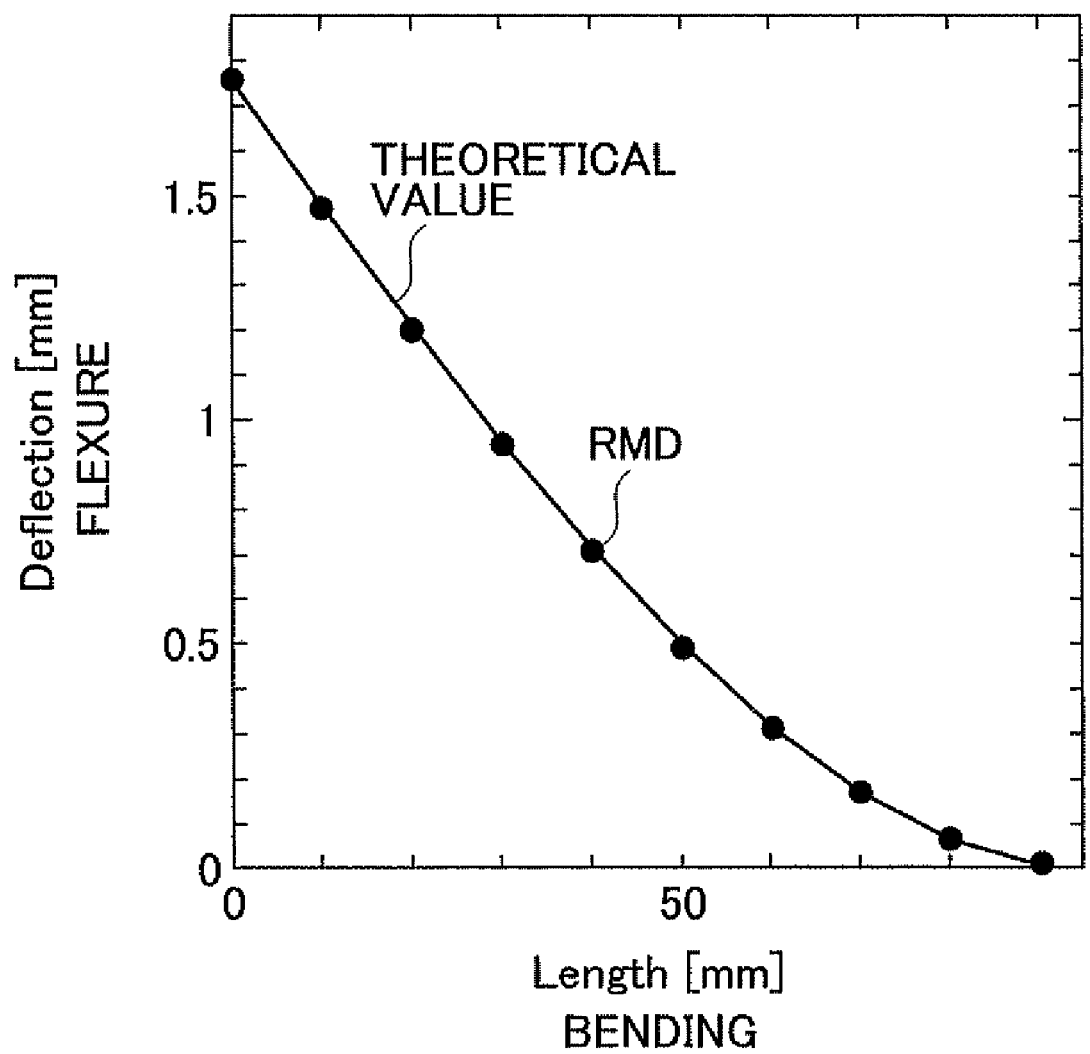
FIG. 7B is an example of a graph illustrating a relationship between the Length of the beam at which flexure is observed and the value of the flexure as Deflection.
Figure 8A:
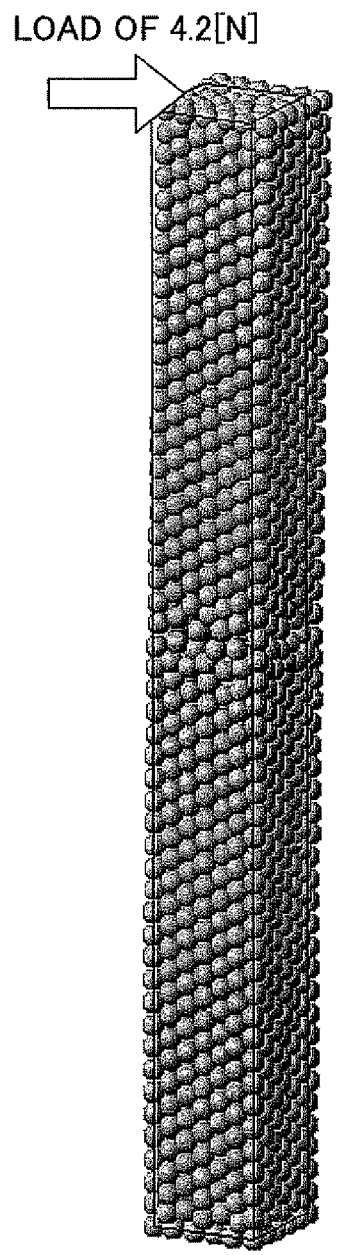
FIG. 8A A beam applied with a load in a lateral direction in a three-dimensional view.
Figure 8B:
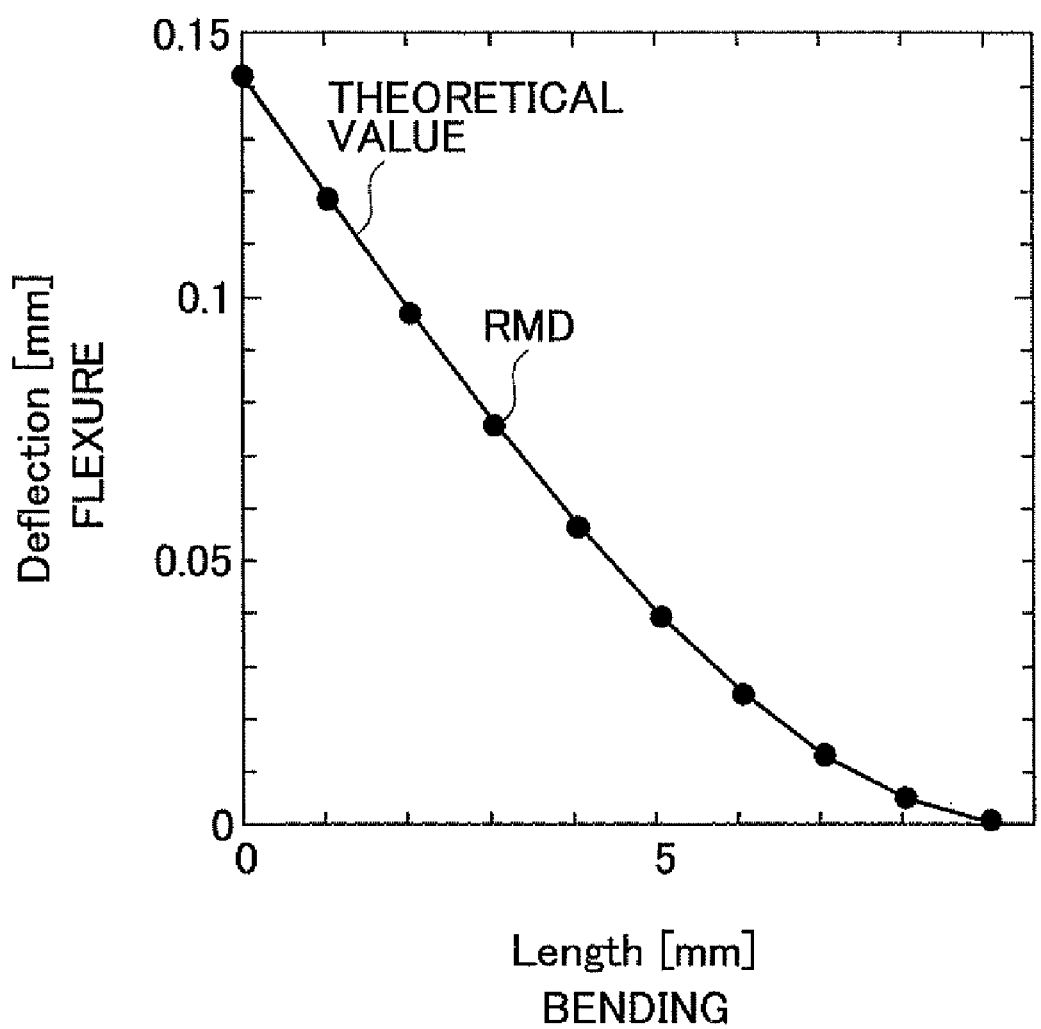
FIG. 8B is an example of a graph illustrating a relationship between the Length of the beam at which flexure is observed and the value of the flexure as Deflection.
Figure 8C:
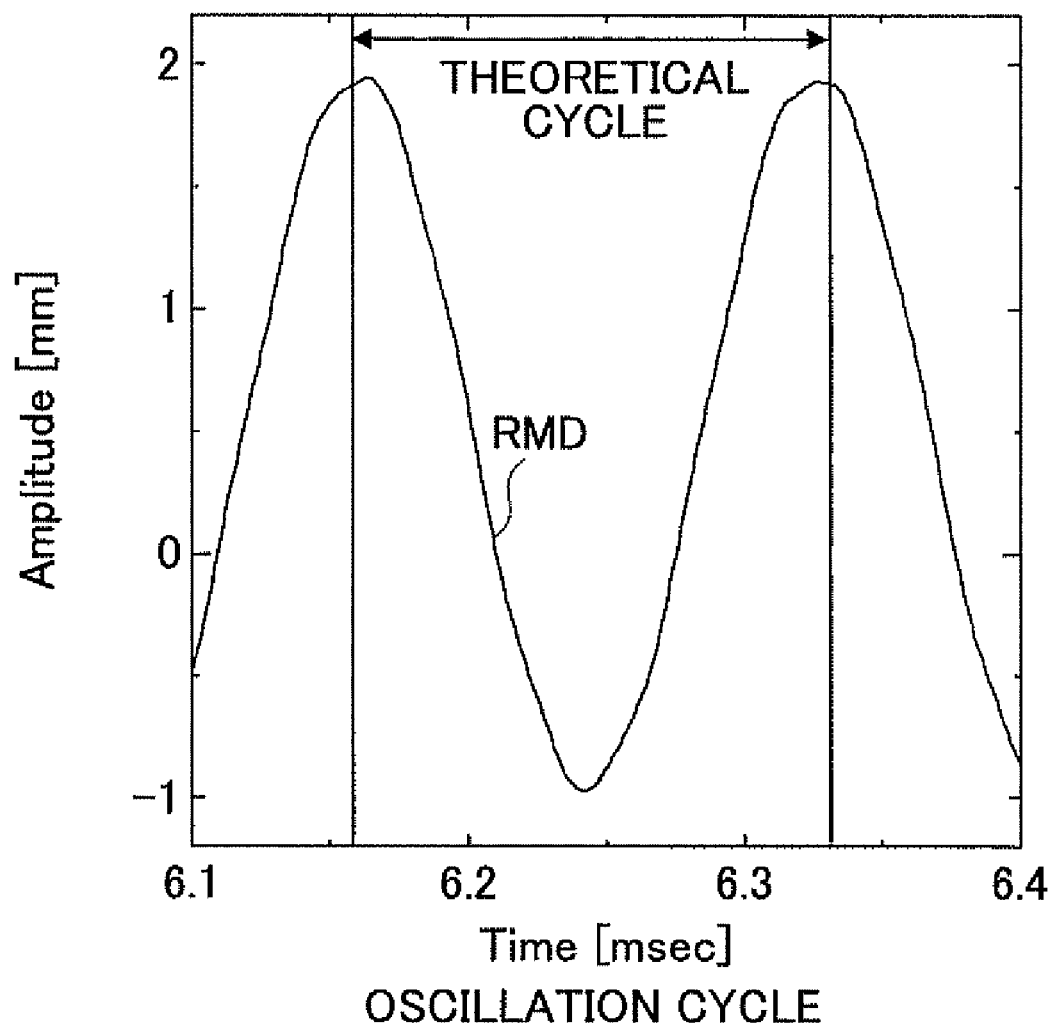
FIG. 8C An example of a graph illustrating a relationship between an oscillation cycle (Time) of a beam and the amplitude (Amplitude) of the oscillation cycle.

FIGS. 7A thru 7C illustrate examples of bending and oscillation of a two-dimensional cantilever beam. FIGS. 8A thru 8C illustrate examples of bending and oscillation of a three-dimensional cantilever beam. FIGS. 7A thru 7C and FIGS. 8A thru 8C described below are examples of figures generated by a screen generating unit 27 described above and output by the output part 22.

FIG. 7A illustrates a beam applied with a load in a lateral direction in a two-dimensional view.

FIG. 7B is an example of a graph illustrating a relationship between the Length of the beam at which flexure is observed and the value of the flexure as Deflection.

FIG. 7C is an example of a graph illustrating a relationship between an oscillation cycle (Time) of a beam and the amplitude (Amplitude) of the oscillation cycle.

FIG. 7A illustrates the beam having the following aspects: a lateral load of 100 [N], a Young's modulus of 208 [GPa], a density of 7800 [kg/m³], and width×height×depth of 10×100×1 [mm]. As illustrated in FIG. 7B, it is possible to know a value obtained by calculation of renormalized molecular dynamics (RMD: points in FIG. 7B) conforms well to a theoretical value (exact solution). It is known from FIG. 7C that a theoretical cycle conforms well to a cycle of RMD (solid lines in FIG. 7C).

FIG. 8B is an example of a graph illustrating a relationship between the Length of the beam at which flexure is observed and the value of the flexure as Deflection.

FIG. 8C is an example of a graph illustrating a relationship between an oscillation cycle (Time) of a beam and the amplitude (Amplitude) of the oscillation cycle.

FIG. 8A illustrates the beam having the following aspects: a lateral load of 4.2 [N], a Young's modulus of 100 [GPa], a density of 7800 [kg/m³], and width×height×depth of 1×10×1[mm]. As illustrated in FIG. 8B, it is possible to know a value obtained by calculation of renormalized molecular dynamics (RMD: points in FIG. 8B) conforms well to a theoretical value (exact solution). It is known from FIG. 8C that a theoretical cycle conforms well to a cycle of RMD (solid lines in FIG. 8C).

According to the present invention, it is possible to stably and properly acquire the physical properties or physical quantities. This makes it possible to realize stabilized calculation without causing a non-physical remaining stress or the like even though a complicated shape is expressed when potential is properly revised using information of the atom arrangement, and reproduction of the physical properties or physical quantities is elaborated.

Said differently, when an intended shape is complicated, insufficiently arranged atoms may be stably calculated in calculations by the molecular dynamics method, and the interatomic potential may be revised so that proper physical quantities may be calculated.

By applying the present invention, it is possible to calculate all classical phenomena other than quantum phenomena in principle such as production of heat by friction in active analyses of mechanisms and elasticity and calculations of destruction. Further, it is possible to broadly apply the present invention in fields of architectural analyses, fluid analyses, motional analyses, optimized designs, electromagnetics and hot matters.

Although there has been described about the embodiment of the present invention, the present invention is not limited to the above embodiment, and various modifications and changes are possible in the scope of the present invention described in the claims.

The present application is based on Japanese Patent Application No. 2007-199646 filed on Jul. 31, 2007. The entire contents of the present application are incorporated by reference.

INDUSTRIAL APPLICABILITY

The present invention is applicable to a molecular simulation method, a molecular simulation device, a molecular simulation program, and a recording medium storing the molecular simulation program, which enable stably and properly acquiring physical properties or physical quantities.

The invention claimed is:

1. A molecular simulation method that acquires physical properties or physical quantities of a predetermined shape using simulation, the molecular simulation method comprising:
arranging atoms in the predetermined shape;
acquiring interatomic potential based on the positions of the arranged atoms and an interatomic bond energy determined based on a Young's modulus; and
carrying out a molecular dynamics calculation based on the acquired interatomic potential, and acquiring the physical properties or the physical quantities,
wherein when acquiring interatomic potential based on the positions of the arranged atoms, there are acquired potential parameters including the interatomic bond energy of the two of the atoms based on a cross-sectional area on which the two of the atoms act between Voronoi points obtained by a Voronoi polyhedron analysis using points of the atoms arranged by the atom arranging part, and the interatomic potential is determined using the acquired potential parameters.

2. The molecular simulation method according to claim 1, wherein when arranging atoms in the predetermined shape, a mesh is generated in the predetermined shape, and the atoms are arranged at intersections of the generated mesh.

3. The molecular simulation method according to claim 1, wherein the interatomic potential is a pair potential using only a distance between two of the atoms as an independent variable.

4. A molecular simulation device that acquires physical properties or physical quantities of a predetermined shape using simulation, the molecular simulation device realized by a computer including a CPU, the molecular simulation device comprising:
an atom arranging part realized by the CPU configured to arrange atoms in the predetermined shape;
an interatomic potential acquiring part realized by the CPU configured to acquire interatomic potential based on positions of the atoms arranged by the atom arranging part and an interatomic bond energy determined based on a Young's modulus; and
a molecular dynamics calculation part realized by the CPU configured to carry out a molecular dynamics calculation based on the interatomic potential acquired by the interatomic potential acquiring part and acquire the physical properties or the physical quantities,
wherein the interatomic potential acquiring part acquires potential parameters including the interatomic bond energy of the two of the atoms based on a cross-sectional area on which the two of the atoms act between Voronoi points obtained by a Voronoi polyhedron analysis using points of the atoms arranged by the atom arranging part, and determines the interatomic potential using the acquired potential parameters.

5. The molecular simulation device according to claim 4, wherein the atom arranging part generates a mesh in the predetermined shape, and arranges the atoms at intersections of the generated mesh.

6. The molecular simulation device according to claim 4, wherein the interatomic potential is a pair potential using only a distance between two of the atoms as an independent variable.

7. A molecular simulation program that acquires physical properties or physical quantities of a predetermined shape using simulation, the molecular simulation program embodied in a non-transitory computer-readable medium and representing a sequence of instructions, which when executed by a computer, the instructions cause the computer to function as:
an atom arranging part configured to arrange atoms in the predetermined shape;

an interatomic potential acquiring part configured to acquire interatomic potential based on positions of the atoms arranged by the atom arranging part and an interatomic bond energy determined based on a Young's modulus; and
a molecular dynamics calculation part configured to carry out a molecular dynamics calculation based on the interatomic potential acquired by the interatomic potential acquiring part and acquire the physical properties or the physical quantities,
wherein the interatomic potential acquiring part acquires potential parameters including the interatomic bond energy of the two of the atoms based on a cross-sectional area on which the two of the atoms act between Voronoi points obtained by a Voronoi polyhedron analysis using points of the atoms arranged by the atom arranging part, and determines the interatomic potential using the acquired potential parameters.

8. The molecular simulation program according to claim 7, wherein the atom arranging part generates a mesh in the predetermined shape, and arranges the atoms at intersections of the generated mesh.

9. The molecular simulation program according to claim 7, wherein the interatomic potential is a pair potential using only a distance between two of the atoms as an independent variable.

* * * * *